United States Patent [19]

Wissner et al.

[11] Patent Number: 4,900,731
[45] Date of Patent: Feb. 13, 1990

[54] ANTIHYPERTENSIVE PHOSPHATE DERIVATIVES

[75] Inventors: Allan Wissner, Ardsley, N.Y.; Robert E. Schaub, Upper Saddle River, N.J.

[73] Assignee: American Cyanamid Company, Stamford, Conn.

[21] Appl. No.: 97,100

[22] Filed: Sep. 15, 1987

Related U.S. Application Data

[63] Continuation of Ser. No. 679,791, Dec. 10, 1984, Pat. No. 4,699,996.

[51] Int. Cl.$^4$ ...................... A61K 31/685; C07F 9/10
[52] U.S. Cl. ...................................... 514/77; 540/450; 540/542; 546/22; 548/112; 558/169
[58] Field of Search ........................ 558/169; 548/112; 546/22; 540/450, 542; 514/77

Primary Examiner—Anton H. Sutto
Attorney, Agent, or Firm—Robert P. Raymond; Philip E. Roux

[57] ABSTRACT

Antihypertensive phosphate derivatives are described having the following formula:

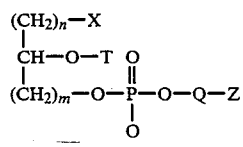

FORMULA 1 wherein n is an integer 1 or 2; m is an integer 1 or 2, and the sum of n and m must be 3; X is selected from the group consisting of $C_1$–$C_{24}$ branched or straight chain alkoxy and substituted phenoxy wherein the substituents are selected from one or more of the group consisting of $C_1$–$C_{20}$ branched or straight chain alkyl, $C_1$–$C_{20}$ branched or straight chain alkoxy, halogen, phenyl and substituted phenyl; T is selected from the group consisting of hydrogen and

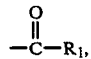

wherein $R_1$ is selected from the group consisting of hydrogen, $C_1$–$C_4$ branched or straight chain alkyl, $C_1$–$C_4$ branched or straight chain alkoxy and $C_1$–$C_4$ branched or straight chain alkylamino, Q is a bivalent radical selected from the group consisting of —($CH_2$)$_p$— and —(CHR)$_p$—, where p is an integer from 2 to 12 and the moiety —(CHR)$_p$— represents an alkylene chain which is substituted by one or more $C_1$–$C_{10}$ alkyl groups or phenyl groups; Z is selected from the group consisting of

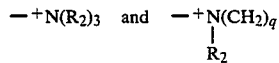

wherein $R_2$ may be the same or different and is selected from the group consisting of hydrogen and $C_1$–$C_4$ branched or straight chain alkyl and q is an integer from 4 to 7.

18 Claims, No Drawings

ANTIHYPERTENSIVE PHOSPHATE DERIVATIVES

This is a continuation of application Ser. No. 679,791 filed Dec. 10, 1984, now U.S. Pat. No. 4,699,996.

BACKGROUND OF INVENTION

This invention pertains to novel phosphate derivatives, and to methods of preparation of such compounds. This invention is also concerned with compositions useful in the treatment of hypertention.

It is estimated that approximately fifteen percent (15%) or more of the adult population in the United States is hypertensive, i.e., having blood pressures greater than or equal to about 160/95 mm Hg. Of that population, approximately one-half is unaware of their hypertensive condition. An untreated hypertensive is at great risk of developing disabling or fatal left ventricular failure, myocardial infarction, cerebral hemorrhage or infarction, and renal failure at an early age. Hypertension is generally considered the most important risk factor predisposing to coronary and cerebral atherosclerosis. However, it is believed that effective medical control of hypertension will prevent or forestall all complications associated with hypertension, and will prolong the life of the hypertensive patient.

Drug therapy for hypertension includes use of diuretics, sympathetic depressants (e.g., α-blockers such as reserpine), vasodilators and finally blockers of sympathetic transmission at the neuroeffector junction (e.g., guanethidine or clonidine).

Among the vasodilators currently employed in hypertension therapy are diazoxide and sodium nitroprusside. Side effects of diazoxide therapy include nausea, vomiting, hyperglycemia and tachycardia. Side effects from sodium nitroprusside therapy include nausea, vomiting, agitation, muscular twitching and cutis anserina if blood pressure is reduced too rapidly. Minoxidil is also often used as a vasodilator in hypertension therapy. However, the side effects of minoxidil include sodium and water retention, and hirsutism. Hydralazine, a mild vasodilator, is also employed. Its side effects include headaches, tachycardia, fluid retention, aggravation of angina, gastrointestinal irritation, lupus-like syndrome, drug fever and psychosis.

Acetyl glyceryl ether phosphocholines have been recognized as having potent biological activity in platelet activation, and in vasoconstricton and vasodilation. See, e.g., U.S. Pat. No. 4,329,302, which issued on May 11, 1982 to Hanahan et al. Such phosphocholines have been identified as both a platelet activation factor (PAF) and an antihypertensive polar renomedullary lipid (APRL). See R. L. Wykle et al., FEBS LETTERS, 141: 29-32 (1982); M. L. Blank et al., BIOCHEMICAL AND BIOPHYSICAL RESEARCH COMMUNICATIONS, 90: 1194-1200 (1979). Antihypertensive phosphocholines do not occur as pre-formed components in the body; rather, such phosphocholines are synthesized by certain cells. See J. Benveniste et al., INT. ARCHS. ALLERGY APPL. IMMUNN., 66 (Supp. 1): 121-126 (1981); E. E. Muirhead, HYPERTENSION, 2: 444-464 (1980). APRL has been described as being accountable in great measure for the endocrine-type antihypertensive action exerted by the renal medullary and the renomedullary interstitial cells. M. L. Blank et at., ID.

BRIEF SUMMARY OF THE INVENTION

The phosphate derivatives of the present invention are selected from those of the formula I:

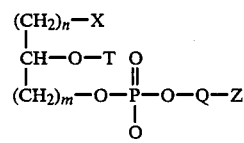

FORMULA 1 wherein n is an integer 1 or 2; m is an integer 1 or 2, and the sum of n and m must be 3; X is selected from the group consisting of $C_1$-$C_{24}$ branched or straight chain alkoxy and substituted phenoxy wherein the substituents are selected from one or more of the group consisting of $C_1$-$C_{20}$ branched or straight chain alkyl, $C_1$-$C_{20}$ branched or straight chain alkoxy, halogen, phenyl and substituted phenyl; T is selected from the group consisting of hydrogen and

wherein $R_1$ is selected from the group consisting of hydrogen, $C_1$-$C_4$ branched or straight chain alkyl, $C_1$-$C_4$ branched or straight chain alkoxy and $C_1$-$C_4$ branched or straight chain alkylamino, Q is a bivalent radical selected from the group consisting of —(CH$_2$)$_p$— and —(CHR)$_p$—, where p is an integer from 2 to 12 and the moiety —(CHR)$_p$— represents an alkylene chain which is substituted by one or more $C_1$-$C_{10}$ alkyl groups or phenyl groups; Z is selected from the group consisting of

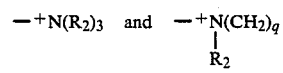

wherein $R_2$ may be the same or different and is selected from the group consisting of hydrogen and $C_1$-$C_4$ branched or straight chain alkyl and q is an integer from 4 to 7; together with their racemic and optically active forms.

DETAILED DESCRIPTION OF THE INVENTION

The compounds of the above formula 1 are prepared as described hereinbelow in Flowsheet A, wherein X, $R_1$ Q, q, p, $R_2$ and Z are as defined hereinabove for formula 1 and $X^1$ is selected from the group consisting of $C_1$-$C_{24}$ branched or straight chain alkyl and substituted phenyl, wherein the substituents are selected from one or more of the group consisting of $C_1$-$C_{20}$ branched or straight chain alkyl, $C_1$-$C_{20}$ branched or straight chain alkoxy, halogen, phenyl and substituted phenyl. The moiety —(CHR)$_p$— represents an alkylene chain substituted by one or more $C_1$-$C_{10}$ alkyl groups or phenyl groups.

According to the sequence of reactions outlined hereinbelow in Flowsheet A, chloroacetic acid 3 is slowly added to a suspension of at least two equivalents sodium hydride in toluene followed by the slow addition of an alcohol or substituted phenol represented by formula 2. The mixture is then refluxed for 20–60 hours and then acidified giving the acid 4 which is reduced with borane in tetrahydrofuran, giving the alcohol 5. Oxidation of 5 with dimethyl sulfoxide —oxalyl chloride at −50° C. to −20° C. gives the aldehyde 6. The reaction of 6 with vinyl magnesium bromide 7 in an ether solvent gives the allylic alcohol 8. Protection of the alcohol group of 8 as a benzyl ether is accomplished by the reaction of 8 with sodium hydride and benzyl bromide in a solvent such as dimethylformamide. The resulting protected compound 9 is then hydroborated and oxidized, giving the alcohol 10. The reaction of 10 with reagents 11a or 11b in an inert solvent in the presence of an amine base such as triethylamine followed by the hydrolysis with a buffer such as aqueous sodium acetate then gives the phosphate 12. The reaction of 12 with amines 13a or 13b in a refluxing inert solvent gives compounds of the formula 14 after treatment with silver carbonate. The benzyl protecting group is removed by hydrogenolysis giving the alcohol 15. The compounds of this invention represented by formula 1 wherein $R_1$ is a $C_1$-$C_4$ alkyl group can be prepared by the reaction of 15 with an anhydride 16 in the presence of a base catalyst such as triethylamine in an inert solvent such as chloroform. The compounds where $R_1$ is a $C_1$-$C_4$ alkoxy group are prepared by the reaction of 15 with a pyrocarbonate 18 in the absence of solvent at 50° to 150° C. The compounds of this invention represented by formula 1 wherein $R_1$ is a $C_1$-$C_4$ alkylamino group can be prepared by the treatment of 15 with an isocyanate 17 in an inert solvent at about 25°-100° C. for 1 to 7 days.

FLOWCHART A

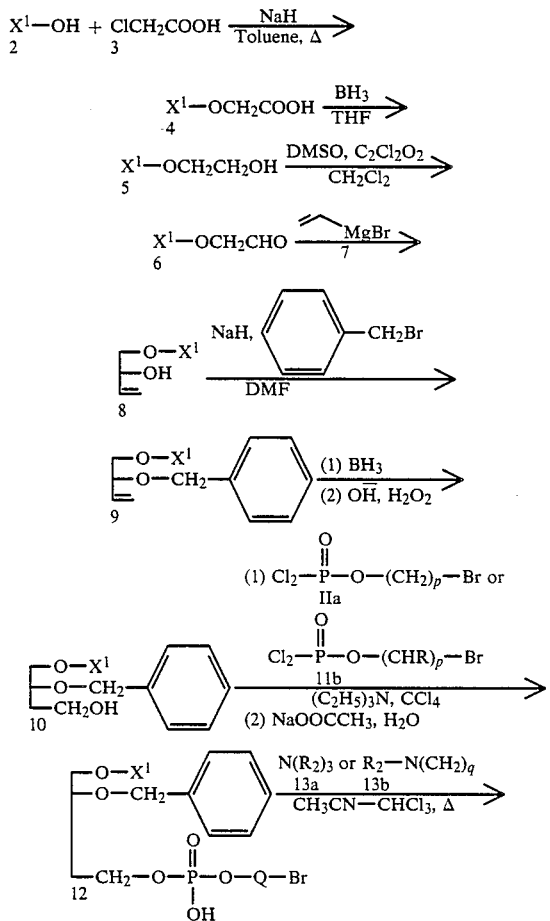

-continued
FLOWCHART A

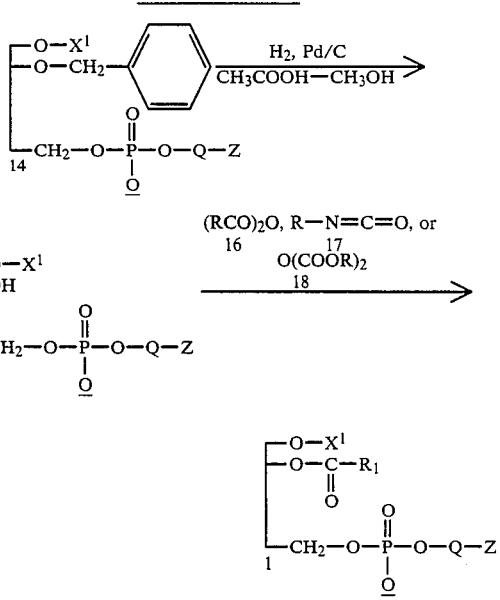

The compounds of this invention encompassed by formula 19 are prepared as described hereinbelow in Flowchart B wherein $X^1$, $R_1$, Q, p, q, $R_2$, Z and the moiety —(CHR)$_p$— are as defined hereinabove and $X^{11}$ is a $C_1$-$C_{24}$ branched or straight chain alkyl group.

According to the sequence of reactions outlined in Flowsheet B the reaction of an alkyl bromide 21 with alcohol 20 using sodium hydride in an inert solvent such as dimethylformamide gives the ether 22. Alternatively ether 25 can be prepared by the alkylation of alcohol or phenol 24 with the bromide 23 using sodium hydride in a inert solvent. The compounds 22 or 25 are then epoxidized using a peracid oxidant such as m-chloroperbenzoic acid in an inert solvent such as methylene chloride. The resulting epoxide 26 is refluxed with acetic acid containing a catalytic amount of a strong acid such as p-toluenesulfonic acid (p-TSA) to give diol 27 after base treatment to remove any acetate groups. The reaction of 27 with trityl chloride in pyridine gives compound 28 in which only the primary hydroxyl group is protected. The reaction of 28 with benzyl bromide and sodium hydride in an inert solvent gives, after acid treatment to remove the trityl group, the compound 29. The reaction of alcohol 29 with reagents 11a and 11b in the presence of an amine base in an inert solvent followed by hydrolysis in a buffer such as aqueous sodium acetate gives the phosphates of formula 30. The reaction of 30 with amines 13a or 13b by refluxing in an inert solvent gives, after treatment with silver carbonate (to remove an amine hydrobromide), the compound 31. Removal of the benzyl protecting group of 31 by hydrogenolysis using a catalyst gives the compound 32. The compounds of this invention represented by formula 19 wherein $R_1$ is a $C_1$-$C_4$ alkyl group can be prepared by the reaction of 32 with an anhydride 16 in the presence of a base catalyst such as triethylamine in an inert solvent such as chloroform. The compounds where $R_1$ is a $C_1$-$C_4$ alkoxy group are prepared by the reaction of 32 with a pyrocarbonate 18 in the absence of solvent at 50° to 150° C. The compounds of this invention represented by formula 19 wherein $R_1$ is a $C_1$-$C_4$ alkylamino group can be prepared by the treatment of 32 with an isocyanate 17 in an inert solvent about 25°–100° C. for 1 to 7 days.

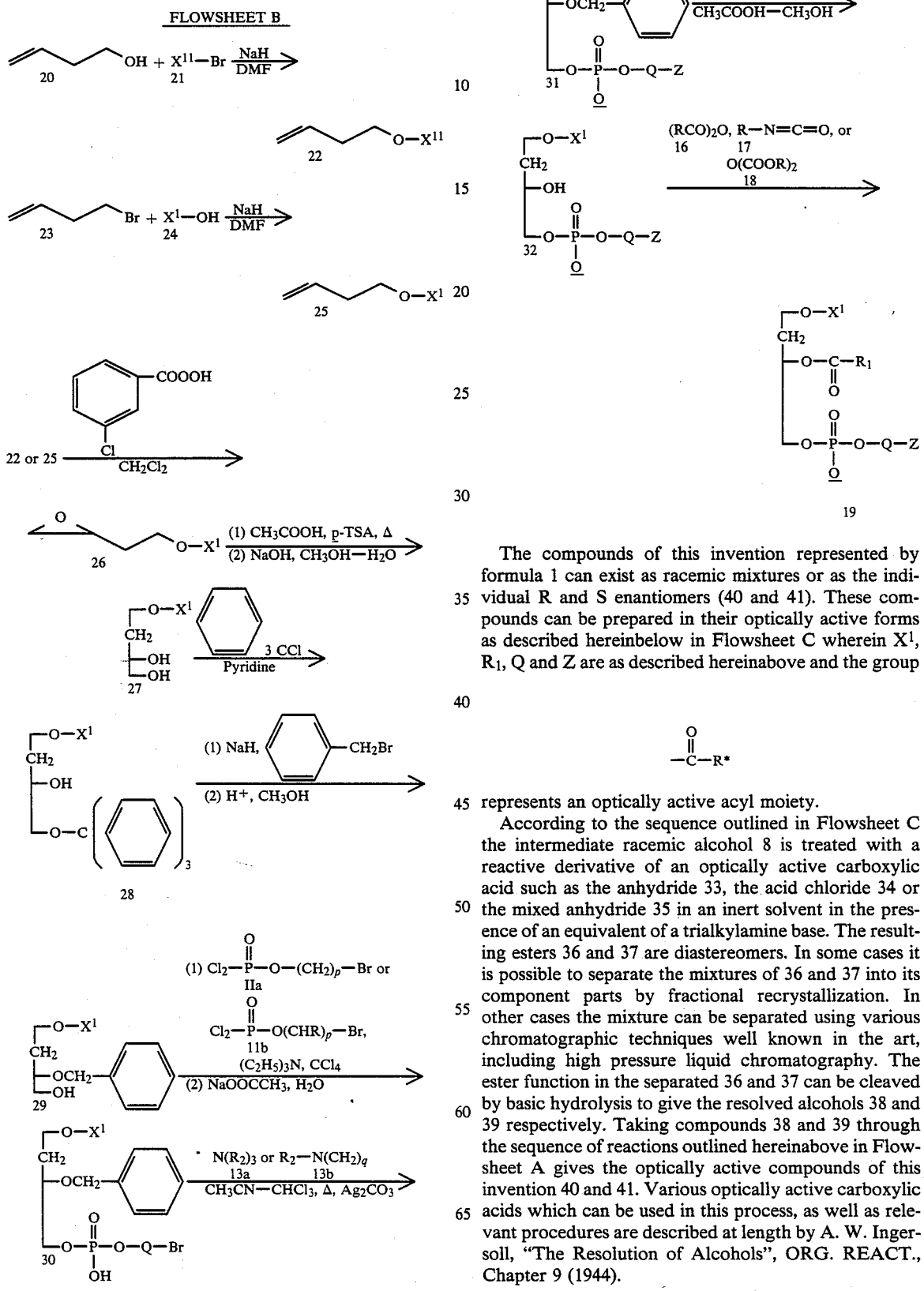

The compounds of this invention represented by formula 1 can exist as racemic mixtures or as the individual R and S enantiomers (40 and 41). These compounds can be prepared in their optically active forms as described hereinbelow in Flowsheet C wherein $X^1$, $R_1$, Q and Z are as described hereinabove and the group $$-\overset{O}{\underset{\|}{C}}-R^*$$

represents an optically active acyl moiety.

According to the sequence outlined in Flowsheet C the intermediate racemic alcohol 8 is treated with a reactive derivative of an optically active carboxylic acid such as the anhydride 33, the acid chloride 34 or the mixed anhydride 35 in an inert solvent in the presence of an equivalent of a trialkylamine base. The resulting esters 36 and 37 are diastereomers. In some cases it is possible to separate the mixtures of 36 and 37 into its component parts by fractional recrystallization. In other cases the mixture can be separated using various chromatographic techniques well known in the art, including high pressure liquid chromatography. The ester function in the separated 36 and 37 can be cleaved by basic hydrolysis to give the resolved alcohols 38 and 39 respectively. Taking compounds 38 and 39 through the sequence of reactions outlined hereinabove in Flowsheet A gives the optically active compounds of this invention 40 and 41. Various optically active carboxylic acids which can be used in this process, as well as relevant procedures are described at length by A. W. Ingersoll, "The Resolution of Alcohols", ORG. REACT., Chapter 9 (1944).

FLOWSHEET C

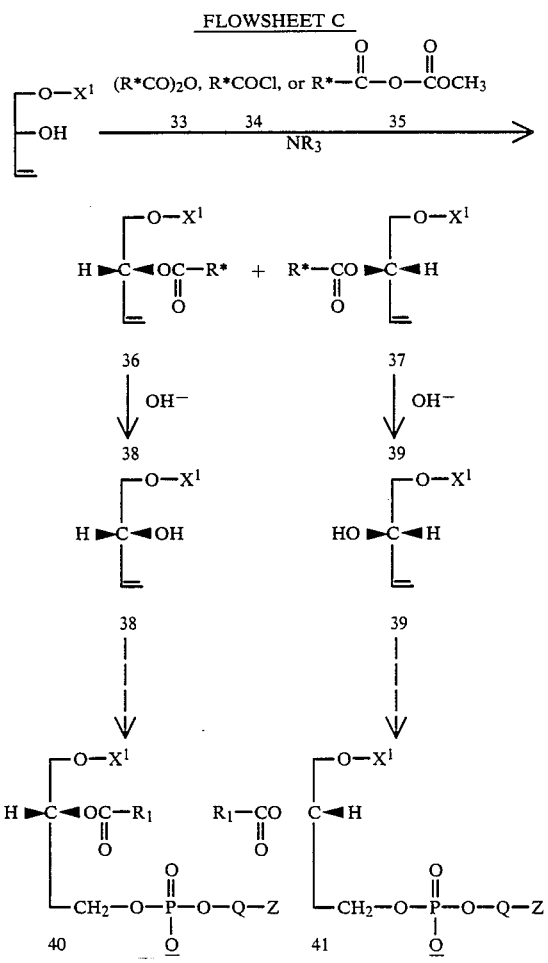

The compounds of this invention represented by formula 19 can exist as racemic mixtures or as the individual R and S enantiomers (46 and 47). These compounds can be prepared in their optically active forms as described hereinbelow in Flowsheet D wherein $X^1$, $R_1$, Q and Z are as described hereinabove and the group

represents an optically active acyl moiety.

According to the sequence outlined in Flowsheet D the intermediate racemic alcohol 29 is treated with a reactive derivative of an optically active carboxylic acid such as the anhydride 33, the acid chloride 34 or the mixed anhydride 35 in an inert solvent in the presence of an equivalent of a trialkylamine base. The resulting esters 42 and 43 are diastereomers. In some cases it is possible to separate the mixture of 42 and 43 into its component parts by fractional recrystallization. In other cases the mixtures can be separated using various chromatographic techniques well known in the art, including high pressure liquid chromatography. The ester function in the separated 42 and 43 can be cleaved by basic hydrolysis to give the resolved alcohols 44 and 45 respectively. Taking compounds 44 and 45 through the sequence of reactions outlined hereinabove in Flowsheet B gives the optically active compounds of this invention 46 and 47. Various optically active carboxylic acids which can be used in this process, as well as relevant procedures are described at length in the aforementioned Ingersole reference.

FLOWSHEET D

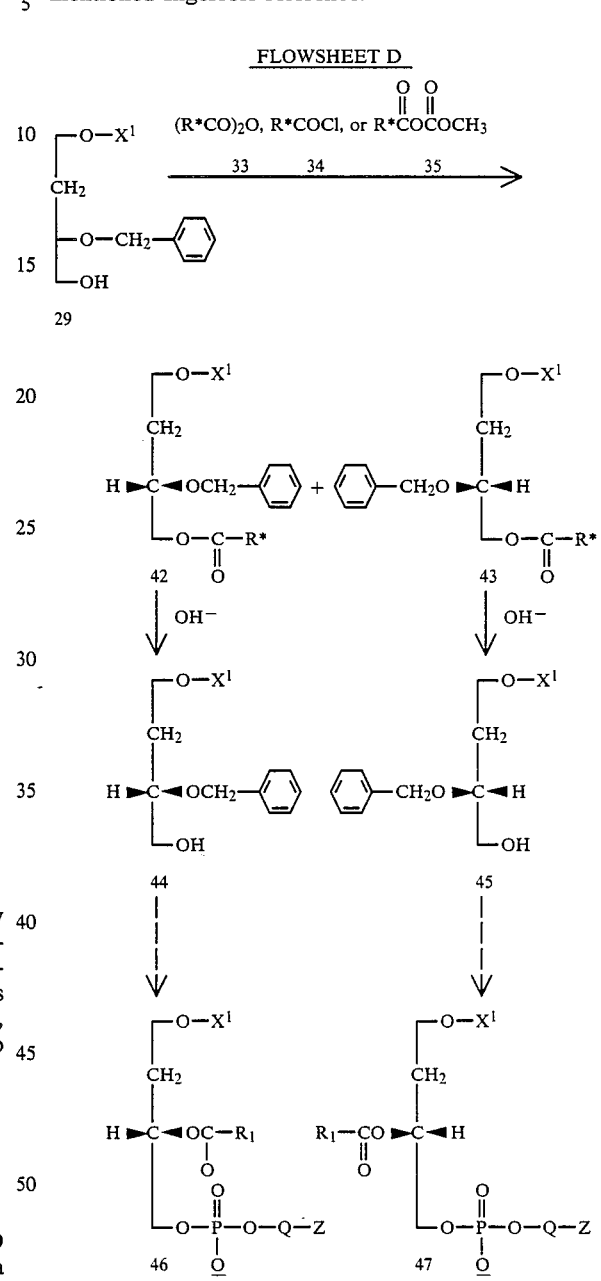

The methods for the preparation of the phosphorous reagents 11a and 11b used to prepare the compounds of this invention are described in detail in a copending application for U.S. Letters Pat. Ser. No. 457,097, filed Jan. 10, 1983, issued on U.S. Pat. No. 4,640,913 on Feb. 3, 1987, which is incorporated herein by reference, as well as in the following references: E. Baer and N. Z. Stanacey, J. BIOL. CHEM., 240, 3754 (1965); A. Eberhard and F. H. Westheimer, J. AMER. CHEM. SOC., 37, 253 (1965). By using such procedures the bromo alcohols of Table I are converted to the indicated phosphorodichlorodate.

TABLE I

| Bromo alcohol | Phosphorodichlorodate |
|---|---|
| 2-bromoethanol | 2-bromoethyl phosphorodichlorodate |
| 3-bromopropanol | 3-bromopropyl phosphorodichlorodate |
| 2-bromopropanol | 2-brompropyl phosphorodichlorodate |
| 2-bromo-1-methylethanol | 2-bromo-1-methylethyl phosphorodichlorodate |
| 4-bromobutanol | 4-bromobutyl phoshorodichlorodate |
| 5-bromopentanol | 5-bromopentyl phosphorodichlorodate |
| 3-bromo-3-methylpropanol | 3-bromo-3-methylpropyl phosphorodichlorodate |
| 3-bromo-2-methylpropanol | 3-bromo-2-methylpropyl phosphorodichlorodate |
| 3-bromo-1-methylpropanol | 3-bromo-1-methylpropyl phosphorodichlorodate |
| 2-bromo-2-phenylethanol | 2-bromo-2-phenylethyl phosphorodichlorodate |
| 3-bromo-2-phenylpropanol | 3-bromo-2-phenylpropyl phosphorodichlorodate |

The methods used for the preparation of certain phenol derivatives (formula 2 of Flowsheet A and formula 24 of Flowsheet B) are described in detail in the aforementioned U.S. Letters Pat. No. 4,640,913 and in the prior art. According to the sequence of reactions outlined in U.S. Pat. No. 4,640,913 an ortho, meta or para substituted bromobenzene is reacted with magnesium in tetrahydrofuran to form the Grignard reagant which in turn is reacted with an alkyl halide in the presence of $Li_2CuCl_4$. The resulting methyl ether is cleaved to the phenol using boron tribromide in an inert solvent such as methylene chloride. Suitable bromo-substituted benzenes are listed in Table XIII, following Example 19 herein. Suitable alkyl halides are listed in Table XIV, also following Example 19 herein. The preparation of certain other phenols is described hereinbelow in Flowsheet E wherein the moiety

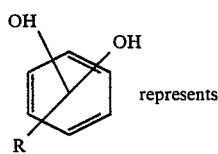

represents a dihydroxy benzene which is substituted with one or more groups selected from those containing of $C_1$-$C_{20}$ branched or straight chain alkyl, $C_1$-$C_{20}$ branched or straight chain alkoxy, halogen, phenyl and substituted phenyl and the moiety $R^1$—Br represents a $C_1$-$C_{20}$ branched or straight chain alkyl bromide.

According to the reaction sequence shown in Flowsheet E, treatment of the diol 48 with sodium hydride in an inert solvent such as dimethylformamide in the presence of an alkyl bromide 49 produces the monoalkylated compound 50 which can be separated from the unreacted 48 and dialkylated product by a combination of distillation and chromatography. The phenols used to prepare some of the compounds of this invention are listed hereinbelow in Table II.

FLOWSHEET E

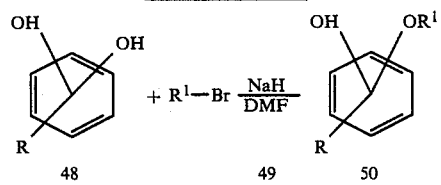

TABLE II 2-hexadecylphenol
4-tetradecylphenol
3-tetradecylphenol
2-tetradecylphenol
3-tridecylphenol
4-dodecylphenol
2-pentadecylphenol
3-dodecyloxy-2-methylphenol The compounds of the present invention are active as hypotensive agents as evidenced by their activity in the following test, the results of which are shown in Table III.

Under ether anesthesia, Weeks type cannulas (Peterson Technics) were surgically implanted in the abdominal aorta and vena cava of spontaneously hypertensive rats (Taconic Farms, Germantown, NY) and passed subcutaneously to the back of the neck where they were exteriorized. The cannulas were filled with saline, plugged and the rats returned to single cages where they were allowed food and water ad libitum.

At least three days following implantation of the cannulas, the rats were weighed and placed in Broome style restraining cages. The plug was removed from the aortic catheter which was connected to an arterial pressure transducer (Statham P23ID) using PE 100 polyethylene tubing and a stepdown connector fabricated from stainless steel hypodermic tubing. Mean arterial blood pressure was obtained by electrical damping of the pulse pressure channel. Heart rate was obtained from a tachograph triggered by the pulse pressure channel. All parameters were monitored on a Grass physiological recorder (Model 7).

The plug was removed from the vena cava catheter and a PE 20 polyethylene tubing extension was added using a piece of stainless steel hypodermic tubing. The other end was terminated with a 27G needle and one ml syringe.

All drugs were dissolved in saline or a mixture of ethanol and saline (25:75 V:V) such that the volume injected intravenously was about 0.1 ml/100 g body weight. All drugs were flushed in with about 0.2 ml saline. Blood pressure was continually monitored both before and after introduction of the test compound.

TABLE III

| Compound | Dose (µg/kg) | No. of Rats | Peak Δ Mean Arterial Blood Pressure(mmHg) |
|---|---|---|---|
| 8-(Acetyloxy)-4-hydroxy-N,N,N—trimethyl-3,5,10-trioxa-4-phosphahexacosan-1-aminium, 4-oxide, hydroxide, inner salt | 10 | 3 | −11.7 |
| | 30 | 3 | −40.1 |
| | 100 | 3 | −77.9 |
| | 300 | 3 | −93.9 |
| 7-(Acetyloxy)-4-hydroxy-N,N,N—trimethyl-3,5,10-trioxa-4-phosphahexacosan-1-aminium, 4-oxide, hydro- | 3 | 6 | −7.6 |
| | 10 | 6 | −18.3 |
| | 30 | 6 | −55.6 |
| | 100 | 6 | −93.1 |

TABLE III-continued

| Compound | Dose (μg/kg) | No. of Rats | Peak Δ Mean Arterial Blood Pressure(mmHg) |
|---|---|---|---|
| oxide, inner salt | 300 | 6 | −100.7 |

When the compounds are employed for the above utility, they may be combined with one or more pharmaceutically acceptable carriers, e.g., solvents, diluents and the like, and may be administered orally in such forms as tablets, capsules, dispersible powders, granules, or suspensions containing, for example, from about 0.05 to 5% of suspending agent, syrups containing, for example, from about 10 to 50% of sugar, and elixirs containing, for example, from about 20 to 50% ethanol, and the like, or parenterally in the form of sterile injectable solutions or suspensions containing from about 0.05 to 5% suspending agent in an isotonic medium. Such pharmaceutical preparations may contain, for example, from about 0.05% up to about 90% of the active ingredient in combination with the carrier, more usually between about 5% and 60% by weight.

The effective dosage of active ingredient employed may vary depending on the particular compound employed, the mode of administration and the severity of the condition being treated. However, in general, satisfactory results are obtained when the compounds of the invention are administered at a daily dosage of from about 0.005 mg to about 100 mg/kg of animal body weight, preferably given in divided doses two to four times a day, or in sustained release form. For most large mammals the total daily dosage is from about 500 μg to about 5,000 mg preferably from about 350 μg to 3,500 mg. Dosage forms suitable for internal use comprise from about 25 μg to 500 mg of the active compound in intimate admixture with a solid or liquid pharmaceutically acceptable carrier. This dosage regimen may be adjusted to provide the optimal therapeutic response. For example, several divided doses may be administered daily or the dose may be proportionally reduced as indicated by the exigencies of the therapeutic situation. A decided practical advantage is that these active compounds may be administered orally as well as by intravenous, intramuscular, or subcutaneous routes. Solid carriers include starch, lactose, dicalcium phosphate, microcrystalline cellulose, sucrose and kaolin, while liquid carriers include sterile water, polyethylene glycols, non-ionic surfactants and edible oils such as corn, peanut and sesame oils, as are appropriate to the nature of the active ingredient and the particular form of administration desired. Adjuvants customarily employed in the preparation of pharmaceutical compositions may be advantageously included, such as flavoring agents, coloring agents, preserving agents, and antioxidants, e.g., vitamin E, ascorbic acid, BHT and BHA.

The preferred pharmaceutical compositions from the stand-point of ease of preparation and administration are solid composition, particularly tablets and hard-filled or liquid-filled capsules. Oral administration of the compounds is preferred.

These active compounds may also be administered parenterally or intraperitoneally. Solutions or suspensions of these active compounds as a free base or pharmacologically acceptable salt can be prepared in water suitably mixed with a surfactant such as hydroxypropylcellulose. Dispersions can also be prepared in glycerol, liquid polyethylene glycols, and mixtures thereof in oils. Under ordinary conditions of storage and use, these preparations should contain a preservative to prevent the growth of microorganisms.

The pharmaceutical forms suitable for injection use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

In addition to the above utilities, some of the compounds of this invention (such as 15 of flowsheet A and 32 of flowsheet B) are useful for the preparation of other compounds of this invention.

The invention will be more fully described in conjunction with the following specific examples which are not to be construed as limiting the scope of the invention.

EXAMPLE 1

(Hexadecyloxy)acetic Acid

To a suspension of 44.52 g of hexane washed 50% sodium hydride in 500 ml of toluene under argon was added, with stirring, a solution of 46.77 g of chloroacetic acid in 200 ml of toluene dropwise over one hour. A solution of 100 g of 1-hexadecanol in 200 ml of toluene was then added dropwise over 15 minutes. The mixture was stirred at reflux for 40 hours, cooled to room temperature and acidified with dilute hydrochloric acid. This mixture was heated with stirring until the solid dissolved. The organic layer was separated while hot, dried, cooled and the solid collected, giving 84.5 g of the desired compound, mp 64°–66° C.

Following the procedure of Example 1, the acetic acid derivatives listed in Table IV are prepared from the indicated hydroxy compounds.

TABLE IV

| Hydroxy Compound | Acetic Acid Derivative |
|---|---|
| n-hexadecanol | n-hexadecyloxy acetic acid |
| n-heptadecanol | n-heptadecyloxy acetic acid |
| n-octadecanol | n-octadecyloxy acetic acid |
| n-pentadecanol | n-pentadecyloxy acetic acid |
| 4-tetradecylphenol | 4-tetradecylphenoxy acetic acid |
| 3-tetradecylphenol | 3-tetradecylphenoxy acetic acid |
| 3-tridecylphenol | 3-tridecylphenoxy acetic acid |
| 3-(dodecyloxy)-2-(methyl)-phenol | [3-(dodecyloxy)-2-(methyl)phenoxy]acetic acid |

EXAMPLE 2

2-(Hexadecyloxy) Ethanol

A solution of 80 g of (hexadecyloxy) acetic acid in 350 ml of tetrahydrofuran was stirred at 0° C. while 798.71 ml of 1M borane in tetrahydrofuran was added dropwise over one hour. When addition was complete the mixture was stirred 2 hours than 50 ml of acetone was added followed by 60 ml of water dropwise. The tetrahydrofuran was allowed to evaporate overnight, then the residue was mixed with water and chloroform and heated to dissolve the solid. The organic layer was separated, dried and the solvent removed. The residue was recrystallized from cold methanol, giving 70.6 g of the desired compound as a white solid, mp 42°–44° C.

Following the procedure of Example 2, the acetic acid derivatives of Table V are reduced with borane and tetrahydrofuran to give the respective substituted ethanol derivatives.

TABLE V

| Acetic Acid Derivative | Substituted Ethanol |
|---|---|
| n-hexadecyloxy acetic acid | 2-(n-hexadecyloxy)ethanol |
| n-heptadecyloxy acetic acid | 2-(n-heptadecyloxy) ethanol |
| n-octadecyloxy acetic acid | 2-(n-octadecyloxy) ethanol |
| n-pentadecyloxy acetic acid | 2-(n-pentadecyloxy) ethanol |
| 4-tetradecylphenoxy acetic acid | 2-(4-tetradecylphenoxy) ethanol |
| 3-tetradecylphenoxy acetic acid | 2-(3-tetradecylphenoxy) ethanol |
| 3-tridecylphenoxy acetic acid | 2-(3-tridecylphenoxy) ethanol |
| [3-(dodecyloxy)-2-(methyl)-phenoxy]acetic acid | 2-[(3-(dodecyloxy)-2-(methyl)phenoxy]ethanol |

EXAMPLE 3

(Hexadecyloxy) Acetaldehyde

A solution of 49.4 g of oxalyl chloride in 900 ml of methylene chloride was cooled to −60° C. and a solution of 60.82 g of dimethyl sulfoxide in 175 ml of methylene chloride was added dropwise over ½ hour so that the temperature did not exceed −50° C. The solution was then warmed to −20° C. and maintained at −20° C. in a dry ice-carbon tetrachloride bath as a solution of 44.6 g of 2-(hexadecyloxy) ethanol in 350 ml of methylene chloride was added over 20 minutes. The mixture was stirred at −20° C. for 20 minutes, 98.2 g of triethylamine was added and the mixture was allowed to warm to room temperature. Water was added, then the organic layer was separated, washed with dilute hydrochloric acid then dilute aqueous sodium bicarbonate until neutral, dried over sodium sulfate and activated charcoal and filtered through silica gel. The solvent was removed at a temperature not exceeding 30° C. The residue was dissolved in petroleum ether, washed with dilute aqueous sodium bicarbonate, dried over sodium sulfate and filtered through magnesium silicate. The filtrate was stored as a solution in a freezer. Immediately prior to use as the starting material in Example 4, the solvent was removed from the filtrate, giving 32 g of the desired compound as a yellow solid.

Following the procedure of Example 3, the substituted ethanol derivatives of Table VI are oxidized to the respective acetaldehyde derivatives.

TABLE VI

| Substituted Ethanol | Acetaldehyde Derivative |
|---|---|
| 2-(n-hexadecyloxy)ethanol | (n-hexadecyloxy) acetaldehyde |
| 2-(n-heptadecyloxy)ethanol | (n-heptadecyloxy) acetaldehyde |
| 2-(n-octadecyloxy)ethanol | (n-octadecyloxy) acetaldehyde |
| 2-(n-pentadecyloxy)ethanol | (n-pentadecyloxy) acetaldehyde |
| 2-(4-tetradecylphenoxy) ethanol | (4-tetradecylphenoxy) acetaldehyde |
| 2-(3-tetradecylphenoxy) ethanol | (3-tetradecylphenoxy) acetaldehyde |
| 2-(3-tridecylphenoxy) ethanol | (3-tridecylphenoxy) acetaldehyde |
| 2-[3-(dodecyloxy)-2-(methyl)-phenoxy] ethanol | [3-(dodecyloxy)-2-(methyl)phenoxy]acetaldehyde |

EXAMPLE 4

1-(Hexadecyloxy)-3-Buten-2-ol

To a stirring mixture of 5.67 g of magnesium in 25 ml of tetrahydrofuran was added 10 drops of dibromoethane as an initiator. After the reaction began another 100 ml of tetrahydrofuran was added followed by the dropwise addition of a solution of 49.85 g of vinyl bromide in 250 ml of tetrahydrofuran at a rate to maintain reflux. After all of the magnesium had reacted, the solution was cooled to 0° C. and a solution of 44.2 g of (hexadecyloxy) acetaldehyde, prepared by the procedure of Example 3, in 175 ml of ether was added dropwise over ½ hour. After 1 hour at room temperature dilute hydrochloric acid was added. The tetrahydrofuran was removed and the residue was extracted with ether. The ether layer was washed with brine, dried and the solvent removed. The residue was purified by HPLC [hexane: ether (9:1), two columns, two passes] giving an oil which was distilled via a Kugelrohr apparatus (185°–190° C., 0.2 mm) giving a colorless oil which solidified on standing to give 20.17 g of the desired compound.

Following the procedure of Example 4, the acetaldehyde derivatives of Table VII are reacted with vinyl magnesium bromide to give the respective 3-buten-2-ol derivatives.

TABLE VII

| Acetaldehyde Derivative | 3-Buten-2-ol |
|---|---|
| (n-hexadecyloxy)acetaldehyde | 1-(n-hexadecyloxy)-3-buten-2-ol |
| (n-heptadecyloxy) acetaldehyde | 1-(n-heptadecyloxy)-3-buten-2-ol |
| (n-octadecyloxy)acetaldehyde | 1-(n-octadecyloxy)-3-buten-2-ol |
| (n-pentadecyloxy) acetaldehyde | 1-(n-pentadecyloxy)-3-buten-2-ol |
| (4-tetradecylphenoxy) acetaldehyde | 1-(4-tetradecylphenoxy)-3-buten-2-ol |
| (3-tetradecylphenoxy) acetaldehyde | 1-(3-tetradecylphenoxy)-3-buten-2-ol |
| (3-tridecylphenoxy) acetaldehyde | 1-(3-tridecylphenoxy)-3-buten-2-ol |
| [3-(dodecyloxy)-2-(methyl)-phenoxy]acetaldehyde | 1-[3-(dodecyloxy)-2-(methyl)phenoxy]-3-buten-2-ol |

EXAMPLE 5

[[[1-[(Hexadecyloxy)methyl]-2-propenyl]oxy]methyl]-benzene

To stirred suspension of 3.35 g of 50% sodium hydride and 10.92 g of benzyl bromide in 75 ml of dimethylformamide was added a solution of 19 g of 1-(hexadecyloxy)-3-buten-2-ol in 75 ml of dimethylformamide. The mixture was stirred overnight, then water was added and the mixture was extracted with ether. The ether extract was dried over magnesium sulfate and activated charcoal and the solvent removed giving an oil. This oil was purified by HPLC [hexane: chloroform (8:1)] and the solvent removed giving 12 g of the desired compound as an oil.

EXAMPLE 6

4-(Hexadecyloxy)-3-(Phenylmethoxy)-1-Butanol

To a solution of 11.5 g of [[[1-[(hexadecyloxy)methyl]-2-propenyl]oxy]methyl]benzene in 50 ml of tetrahydrofuran was added dropwise, at 0° C., 57.12 ml of 1M borane in tetrahydrofuran. After stirring at room temperature for 3 hours the excess borane was destroyed by the addition of water. The mixture was cooled in an ice bath, 100 ml of 3N sodium hydroxide was added followed by 100 ml of 30% hydrogen peroxide and after 10 minutes the mixture was stirred for ½ hour at room temperature and then diluted with ether. The ether layer was separated, washed with brine, then saturated sodium bisulfite, dried over magnesium sulfate and the solvent removed. The residue was purified by HPLC [hexane: ethyl acetate (9:1)] giving 7.8 g of the desired compound as an oil.

Following the procedures of Examples 5 and 6 the 3-buten-2-ol derivatives of Table VIII are alkylated with benzyl bromide and then hydroborated to give the corresponding 1-butanol derivatives.

TABLE VIII

| 3-Buten-2-ol | 1-Butanol Derivative |
| --- | --- |
| 1-(n-hexadecyloxy)-3-buten-2-ol | 4-(n-hexadecyloxy)-3-(phenylmethoxy)-1-butanol |
| 1-(n-heptadecyloxy)-3-buten-2-ol | 4-(n-heptadecyloxy)-3-(phenylmethoxy)-1-butanol |
| 1-(n-octadecyloxy)-3-buten-2-ol | 4-(n-octadecyloxy)-3-(phenylmethoxy)-1-butanol |
| 1-(n-pentadecyloxy)-3-buten-2-ol | 4-(n-pentadecyloxy)-3-(phenylmethoxy)-1-butanol |
| 1-(4-tetradecylphenoxy)-3-buten-2-ol | 4-(4-tetradecylphenoxy)-3-(phenylmethoxy)-1-butanol |
| 1-(3-tetradecylphenoxy)-3-buten-2-ol | 4-(3-tetradecylphenoxy)-3-(phenylmethoxy)-1-butanol |
| 1-(3-tridecylphenoxy)-3-buten-2-ol | 4-(3-tridecylphenoxy)-3-(phenylmethoxy)-1-butanol |
| 1-[3-(dodecyloxy)-2-(methyl)phenoxy]-3-buten-2-ol | 4-[3-(dodecyloxy)-2-(methyl)phenoxy]-3-(phenylmethoxy)-1-butanol |

EXAMPLE 7

4-(Hexadecyloxy)-3-(Phenylmethoxy)Butyl Phosphoric Acid, 2-Bromoethyl Ester

To a solution of 7.3 g of 4-(hexadecyloxy)-3-(phenylmethoxy)-1-butanol in 160 ml of carbon tetrachloride was added with stirring 7.34 g of 2-bromoethyl phosphorodichlorodate and 3.07 g of triethylamine. The mixture was stirred 1.5 hours, then filtered through diatomaceous earth and the solvent removed. The residue was added to a mixture of 300 ml of 0.5M sodium acetate and 300 ml of tetrahydrofuran for 3 hours. The tetrahydrofuran was removed, the aqueous solution was acidified with hydrochloric acid and extracted with ether. The ether solution was washed with brine, dried and the solvent removed giving the desired compound as a yellow oil which was used without further purification in Example 8.

EXAMPLE 8

4-Hydroxy-N,N,N-Trimethyl-8-(Phenylmethoxy)-3,5,10-Trioxa-4-Phosphahexacosan-1-Aminium, 4-Oxide, Hydroxide, Inner Salt A mixture of 10.54 g of 4-(hexadecyloxy)-3-(phenylmethoxy)butyl phosphoric acid, 2-bromoethyl ester, 100 ml of acetonitrile, 90 ml of chloroform and 50 ml of trimethylamine was refluxed for 20 hours, then the solvent was removed. The residue was dissolved in 100 ml of methanol, 2.7 g of silver carbonate was added and the mixture was stirred 2 hours then filtered through diatomaceous earth. The solvent was removed and the residue chromatographed on silica gel, eluting first with chloroform:methanol (7:3) and then with chloroform:methanol:water (70:30:5) to remove the product. The solvent was removed, the residue mixed with ether, the ether decanted and the precipitate dried in vacuo, giving 6.31 g of the desired compound as a white powder, mp 60° C. (softening).

EXAMPLE 9

4,8-Dihydroxy-N,N,N-Trimethyl-3,5,10-Trioxa-4-Phosphahexacasan-1-Aminium, 4-Oxide, Hydroxide, Inner Salt A mixture of 5.6 g of 4-hydroxy-N,N,N-trimethyl-8-(phenylmethoxy)-3,5,10-trioxa-4-phosphahexcosan-1-aminium, 4-oxide, hydroxide inner salt, 35 ml of acetic acid, 35 ml of methanol and 0.5 g of 5% palladium on carbon was shaken in a Parr apparatus under hydrogen for 17 hours, then filtered through diatomaceous earth and the solvent removed. The resulting 4.7 g of the desired compound was used without further purification in Example 10.

EXAMPLE 10

8-(Acetyloxy)-4-Hydroxy-N,N,N-Trimethyl-3,5,10-Trioxa-4-Phosphahexacosan-1-Aminiun, 4-Oxide, Hydroxide, Inner Salt A mixture of 4.5 g of 4,8-dihydroxy-N,N,N-trimethyl-3,5,10-trioxa-4-phosphahexacosan-1-aminium, 4-oxide, hydroxide, inner salt, 23.17 g of acetic anhydride, 9.19 ml of triethylamine and 300 ml of chloroform was refluxed for 4 hours and then allowed to stand overnight. The solvent and excess anhydride were removed at reduced pressure. The residue was chromatographed on 250 ml of silica gel, eluting first with chloroform:methanol (7:3) and then with chloroform: methanol:water (70:30:5) to elute the product. The solvent was removed, the residue dissolved in chloroform and filtered. The solvent was removed, ether was added and the solid collected, giving 3.6 g of the desired product as a white powder, mp 68° C. (softening).

EXAMPLE 11

1-(3-Butenyloxy)Hexadecane

A 73.22 g portion of 50% sodium hydride in oil was washed twice with 100 ml portions of hexanes under an argon atmosphere. A 1250 ml portion of dry dimethylformamide was added. The mixture was stirred as a solution of 100 g of 3-buten-1-ol in 300 ml of dimethylformamide was added dropwise over 1.5 hours. The mixture was stirred for an additional hour, then 423.5 g of n-hexadecyl bromide was added dropwise. The mixture was cooled in a water bath to keep the temperature below 40° C. as the mixture was stirred under argon overnight. Water was added to destroy the excess sodium hydride, then the mixture was diluted with 1500 ml of water and the oil was extracted by four ether extractions. The ether extracts were combined, washed twice with saline, dried and the solvents removed giving an oil. This oil was purified by evaporative distillation giving 131.6 g of the desired compound as a pale yellow oil.

EXAMPLE 12

[2-(Hexadecyloxy)Ethyl]Oxirane

To a solution of 100 g of 1-(3-butenyloxy)hexadecane in 640 ml of methylene chloride was added portionwise 69 g of m-chloroperbenzoic acid. The mixture was stirred under argon for 72 hours and then the solvents were removed. The residue was dissolved in ether and washed with saturated aqueous sodium bicarbonate, dried and evaporated to an oil. This oil was distilled (140°-150° C., 0.05 mm Hg) giving 83.4 g of the desired compound as an oil.

Following the procedure of Example 11, the alkyl bromides (1-bromohexadecane, 1-bromoheptadecane, 1-bromooctadecane and 1-bromopentadecane) are used to alkylate 1-hydroxy-3-butene. The resulting compounds are then epoxidized as described in Example 12 to give the respective oxiranes listed in Table IX. Other suitable alkyl bromides are listed in Table XIV, following Example 19 herein. By a similar procedure, and by way of example, some of the phenols of Table II are alkylated with 1-bromo-3-butene and the resulting compounds are epoxidized as described in Example 12 to give the other oxiranes of Table IX.

TABLE IX

| Oxiranes |
| --- |
| [2-(n-hexadecyloxy)ethyl]oxirane |
| [2-(n-heptadecyloxy)ethyl]oxirane |
| [2-(n-octadecycloxy)ethyl]oxirane |
| [2-(n-pentadecyloxy)ethyl]oxirane |
| [2-(2-tetradecylphenoxy)ethyl]oxirane |
| [2-(3-tetradecylphenoxy)ethyl]oxirane |
| [2-(3-tridecylphenoxy)ethyl]oxirane |
| [2-[2-(dodecyloxy)-2-(methyl)phenoxy]ethyl]oxirane |

EXAMPLE 13

4-(Hexadecyloxy)-1,2-Butanediol

A solution of 40 g of [2-(hexadecyloxy)ethyl] oxirane in 270 ml of glacial acetic acid containing 0.265 g of p-toluenesulfonic acid was stirred at reflux for 4.5 hours. The acetic acid was removed, the residue dissolved in toluene the toluene removed and this residue dissolved in 300 ml of methanol. A solution of 17.9 g of sodium hydroxide in 18.5 ml of water was added, the mixture was stirred ½ hour and the solvent removed. The solid was dissolved in a mixture of ether and water. The ether layer was washed twice with saline, dried and filtered. The filtrate was warmed to dissolve the solid which formed, then concentrated to about 400 ml and allowed to stand at room temperature. Petroleum ether was added and the resulting solid collected, giving 32 g of the desired compound, mp 60°-61° C.

By the procedure of Example 13 the oxiranes of Table X are converted to their respective 1,2-butanediol derivatives.

TABLE X

| Oxirane | 1,2-Butanediol |
| --- | --- |
| [2-(n-hexadecyloxy)ethyl]oxirane | 4-(n-hexadecyloxy)1,2-butanediol |
| [2-(n-heptadecyloxy)ethyl]oxirane | 4-(n-heptadecyloxy)-1,2-butanediol |
| [2-(n-octadecyloxy)ethyl]oxirane | 4-(n-octadecyloxy)-1,2-butanediol |
| [2-(n-pentadecyloxy)ethyl]oxirane | 4-(n-pentadecyloxy)-1,2-butanediol |
| [2-(2-tetradecylphenoxy)ethyl]oxirane | 4-(4-tetradecylphenoxy)-1,2-butanediol |
| [2-(3-tetradecylphenoxy)ethyl]oxirane | 4-(3-tetradecylphenoxy)-1,2-butanediol |
| [2-(3-tridecylphenoxy)ethyl]oxirane | 4-(3-tridecylphenoxy)-1,2,-butanediol |
| [2-[2-(dodecyloxy)-2-(methyl)phenoxy]ethyl]oxirane | 4-[2-(dodecyloxy)-2-(methyl)phenoxy]-1,2-butanediol |

EXAMPLE 14

4-(Hexadecyloxy)-1-(Triphenylmethoxy)-2-Butanol

To a solution of 30 g of 4-(hexadecyloxy)-1,2,-butanediol in 135 ml of dry pyridine was added 37.95 g of trityl chloride. The solution was allowed to stand under argon for 24 hours and was then poured into 700 ml of ice water and extracted three times with ether. The ether extracts were combined, washed with ice cold 5% hydrochloric acid, then saturated salt solution, dried and evaporated to dryness. The residue was mixed with petroleum ether, allowed to stand 72 hours, the solid removed and the mother liquor taken to dryness, giving 56.65 g of the desired compound of an oil.

By the procedure of Example 14, the 1,2-butanediols of Table XI are mono-protected with trityl chloride in pyridine giving the respective trityl compounds.

TABLE XI

| 1,2-Butanediol | Trityl Derivative |
| --- | --- |
| 4-(n-hexadecyloxy)-1,2-butanediol | 4-(n-hexadecyloxy)-1-(triphenylmethoxy)-2-butanol |
| 4-(n-heptadecyloxy)-1,2-butanediol | 4-(n-heptadecyloxy)-1-(triphenylmethoxy)-2-butanol |
| 4-(n-octadecyloxy)-1,2-butanediol | 4-(n-octadecyloxy)-1-(triphenylmethoxy)-2-butanol |
| 4-(n-pentadecyloxy)-1,2-butanediol | 4-(n-pentadecyloxy)-1-(triphenylmethoxy)-2-butanol |
| 4-(4-tetradecylphenoxy)-1,2--butanediol | 4-(4-tetradecylphenoxy)-1-(triphenylmethoxy)-2-butanol |
| 4-(3-tetradecylphenoxy)-1,2-butanediol | 4-(3-tetradecylphenoxy)-1-(triphenylmethoxy)-2-butanol |
| 4-(3-tridecylphenoxy)-1,2-butanediol | 4-(3-tridecylphenoxy)-1-(triphenylmethoxy)-2-butanol |
| 4-[2-(dodecyloxy)-2-(methyl)phenoxy]-1,2-butanediol | 4-[2-(dodecyloxy)-2-(methyl)phenoxy]-1-(triphenylmethoxy)-2-butanol |

EXAMPLE 15

4-(Hexadecyloxy)-2-(Phenylmethoxy)-1-Butanol

To a suspension of 6.17 g of 50% sodium hydride (washed with hexanes) in 245 ml of dry dimethylformamide was added 19.45 g of benzyl bromide at 0° C. A solution of 56.65 g of 4-(hexadecyloxy)-1-(triphenylmethoxy)-2-butanol in 60 ml of dimethylformamide was added dropwise with stirring at 0° C. under argon. The mixture was stirred overnight at room temperature, then poured into 1000 ml of iced water and extracted with petroleum ether. The organic phase was dried, the solvent removed and the residue dissolved in a mixture of 235 ml of methanol and 125 ml of tetrahydrofuran. A 500 mg portion of p-toluene sulfonic acid was added, the mixture was allowed to stand overnight and then the solvent was removed. The residue was dissolved in petroleum ether, washed with saturated aqueous sodium bicarbonate, dried and the solvent removed giving an oil. This oil was again subjected to treatment with p-toluenesulfonic acid in the solvent system described above, again giving an oil which was purified by HPLC, giving 23 g of the desired compound as an oil.

By the procedure described in Example 15, the trityl derivatives of Table XII are alkylated with benzyl bromide and then deprotected to give the 1-butanol derivatives.

TABLE XII

| Trityl Derivative | 1-Butanol |
| --- | --- |
| 4-(n-hexadecyloxy)-1-(triphenylmethoxy)-2-butanol | 4-(n-hexadecyloxy)-2-(phenylmethoxy)-1-butanol |
| 4-(n-heptadecyloxy)-1-(triphenylmethoxy)-2-butanol | 4-(n-heptadecyloxy)-2-(phenylmethoxy)-1-butanol |
| 4-(n-octadecyloxy)-1-(triphenylmethoxy)-2-butanol | 4-(n-octadecyloxy)-2-(phenylmethoxy)-1-butanol |
| 4-(n-pentadecyloxy)-1-(triphenylmethoxy)-2-butanol | 4-(n-pentadecyloxy)-2-(phenylmethoxy)-1-butanol |
| 4-(4-tetradecylphenoxy)-1-(triphenylmethoxy)-2-butanol | 4-(4-tetradecylphenoxy)-2-(phenylmethoxy)-1-butanol |
| 4-(3-tetradecylphenoxy)-1-(triphenylmethoxy)-2-butanol | 4-(3-tetradecylphenoxy)-2-(phenylmethoxy)-1-butanol |
| 4-(3-tridecylphenoxy)-1-(triphenylmethoxy)-2-butanol | 4-(3-tridecylphenoxy)-2-(phenylmethoxy)-1-butanol |
| 4-[2-(dodecyloxy)-2-(methyl)-phenoxy]-1-(triphenylmethoxy)-2-butanol | 4-[2-(dodecyloxy)-2-(methyl)phenoxy]-2-(phenylmethoxy)-1-butanol |

EXAMPLE 16

2-Bromoethyl 4-(Hexadecyloxy)-2-(Phenylmethoxy) Phosphoric Acid, Butyl Ester

To a solution of 412.98 g of phosphorous oxychloride in 910 ml of carbon tetrachloride was added 224.4 g of 2-bromoethanol dropwise over 30 minutes. The mixture was stirred overnight. The solvent was removed and the residue evaporated twice from toluene. The resulting oil was distilled giving 167 g of 2-bromoethyl phosphorodichlorodate.

To a solution of 8.05 g of 2-bromoethyl phosphorodichlorodate in 200 ml of carbon tetrachloride, cooled and stirred at 0° C. under an argon atmosphere, was added dropwise 18.6 ml of triethylamine. A solution of 10 g of 4-(hexadecyloxy)-2-(phenylmethoxy)-1-butanol in 10 ml of carbon tetrachloride was added dropwise and the mixture was stirred overnight. A 200 ml portion of toluene was added, the mixture was filtered through diatomaceous earth and the solvent was removed. To the residual syrup was added 140 ml of tetrahydrofuran and 140 ml of 0.5M sodium acetate solution. This mixture was stirred for 4 hours, then the tetrahydrofuran was removed and the aqueous remainder acidified with 1 N hydrochloric acid. This mixture was extracted three times with ether. The ether extracts were combined, washed twice with saturated salt solution, dried with magnesium sulfate and activated charcoal, filtered and evaporated to an oil. This oil was purified by chromatography on magnesium silicate, giving 11.84 g of the desired compound as a yellow syrup.

EXAMPLE 17

4-Hydroxy-N,N,N-Trimethyl-7-(Phenylmethoxy)-3,5,10-Trioxa-4-Phosphahexacosan-1-Aminium, 4-Oxide, Hydroxide Inner Salt A solution of 11.7 g of 2-bromoethyl-4-(hexadecyloxy)-2-(phenylmethoxy)phosphoric acid, butyl ester in a mixture of 125 ml of acetonitrile, 112 ml of chloroform and 50 ml of anhydrous trimethylamine was refluxed in an oil bath for 16 hours. The solvent was removed and the residue dissolved in 100 ml of methanol. A 2.8 g portion of silver carbonate was added and the mixture was stirred under argon for 13 hours, then filtered through diatomaceous earth and washed with methanol. The mother liquor was evaporated to a foam which was triturated with ether giving a white solid. After stirring one hour this solid was collected, washed with cold ether and dried in vacuo, giving 9.33 g of the desired compound mp 182°-186° C.

EXAMPLE 18

4,7-Dihydroxy-N,N,N-Trimethyl-3,5,10-Trioxa-4-Phosphahexacosan-1-Aminium, 4-Oxide, Hydroxide, Inner Salt A solution of 8.8 g of 4-Hydroxy-N,N,N-trimethyl-7-(phenylmethoxy)-3,5,10-trioxa-4-phosphahexacosan-1-aminium, 4-oxide, hydroxide, inner salt in 60 ml of glacial acetic acid and 60 ml of methanol was hydrogenated in a Parr shaker with 900 mg of 5% palladium on carbon at an initial pressure of 25 psi of hydrogen for 18 hours. The mixture was filtered through diatomaceous earth, washed with methanol and the mother liquor taken to dryness. The residue was evaporated twice from toluene, giving a glass. This glass was stirred with ether giving a white solid which was collected, giving 7.5 g of the desired compound, mp 95°-100° C.

EXAMPLE 19

7-(Acetyloxy)-4-Hydroxy-N,N,N-Trimethyl-3,5,10-Trioxa-4-Phosphahexacosan-1-Aminium, 4-Oxide, Hydroxide, Inner Salt A mixture of 5 g of 4,7-dihydroxy-N,N,N-trimethyl-3,5,10-trioxa-4-phosphahexacosan-1-aminium, 4-oxide, hydroxide, inner salt in 500 ml of dry chloroform, 25 g of acetic anhydride and 10.2 g of triethylamine was stirred at reflux in an oil bath under argon for 4 hours. The solvents were removed and the residue evaporated twice from toluene. The resulting syrup was dissolved in ether and stored at 0° C. overnight then purified by chromatograph as described in Example 10, giving 2.88 g of the desired product, mp 135° C.

Following the procedures of Examples 7 and 16 the 1-butanol derivatives of Tables VIII and XII are reacted with the phosphorous reagents of Table I. The resulting compounds are then reacted with triethylamine, dimethylamine or methylamine according with the procedures described in Example 8 and 17. Suitable alkyl amines which can be used according to the procedures described in Examples 8 and 17 are listed in following Table XV. The benzyl group is then removed by hydrogenolysis as described in detail in Examples 9 and 18. The resulting compounds are then reacted with a $C_1$–$C_4$ anhydride or with formic acid as described in Examples 9 and 19 and in copending application for U.S. Letters Pat. Ser. No. 457,097, filed Jan. 10, 1983 to give the compounds of this invention listed hereinbelow as racemic mixtures and as the individual optical isomers.

TABLE XIII

| Substituted Bromobenzenes |
| --- |
| p-bromoanisole |
| m-bromoanisole |
| o-bromoanisole |

TABLE XIV

| Alkyl Halides |
| --- |
| 1-undecylbromide |
| 1-dodecylbromide |
| 1-tridecylbromide |
| 1-tetradecylbromide |
| 1-pentadecylbromide |
| nonadecyl iodide |
| heptadecyl iodide |
| hexadecyl iodide |
| pentadecyl iodide |
| tetradecyl iodide |
| tridecyl iodide |
| 2-methylhexadecyl iodide |
| 3-ethylpentadecyl iodide |
| 2,4-dimethylhexadecyl iodide |

TABLE XV

| Alkyl Amines |
| --- |
| trimethyl amine |
| dimethyl amine |

In addition to the procedures described above for the preparation of the compounds of this invention, other relevant procedures are described in a co-pending application (457,097, filed Jan. 10, 1983).

What is claimed is:

1. A method of treating hypertension in a warm-blooded animal which comprises administering to said animal an effective amount of a compound, including the individual R and S enantiomers and racemic mixture, represented by the formula:

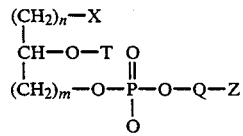

FORMULA 1 wherein n is an integer 1 or 2; m is an integer 1 or 2, and the sum of n and m must be 3; X is selected from the group consisting of $C_1$–$C_{24}$ branched or straight chain alkoxy and substituted phenoxy wherein the substituents are selected from one or more of the group consisting of $C_1$–$C_{20}$ branched or straight chain alkyl, $C_1$–$C_{20}$ branched or straight chain alkoxy, halogen, phenyl and substituted phenyl; T is selected from the group consisting of hydrogen and

wherein $R_1$ is selected from the group consisting of hydrogen, $C_1$–$C_4$ branched or straight chain alkyl, $C_1$–$C_4$ branched or straight chain alkoxy and $C_1$–$C_4$ branched or straight chain alkylamino, Q is a bivalent radical selected from the group consisting of —(CH$_2$)$_p$— and —(CHR)$_p$—, where p is an integer from 2 to 12 and the moiety —(CHR)$_p$— represents an alkylene chain which is substituted by one or more $C_1$–$C_{10}$ alkyl groups or phenyl groups; and Z is selected from the group consisting of

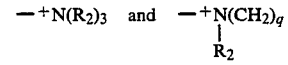

wherein $R_2$ may be the same or different and is selected from the group consisting of hydrogen and $C_1$–$C_4$ branched or straight chain alkyl and q is an integer from 4 to 7.

2. A method of treating hypertension in a warm-blooded animal which comprises administering to said animal an effective amount of a compound, including the individual R and S enantiomers and racemic mixture, represented by the formula:

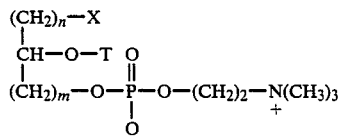

wherein n is an integer 1 or 2; m is an integer 1 or 2, and the sum of n and m must be 3; X is selected from n-hexadecyloxy, n-heptadecyloxy, n-octadecyloxy, n-pentadecyloxy, 4-tetradecylphenoxy, 3-tetradecylphenoxy, 2-tetradecylphenoxy, 3-tridecylphenoxy and 3-dodecyloxy-2-methyl phenoxy; and T is selected from hydrogen and acetyl.

3. A method of treating hypertension in a warm-blooded animal which comprises administering to said animal an effective amount of a compound, including the individual R and S enantiomers and racemic mixture, represented by the formula:

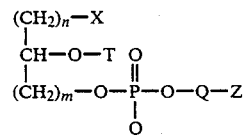

wherein n is an integer 1 or 2; m is an integer 1 or 2, and the sum of n and m must be 3; X is selected from $C_{11}$–$C_{19}$ alkoxy and substituted phenoxy wherein the substituents are selected from one or more of $C_1$–$C_{19}$ alkyl and $C_{11}$–$C_{15}$ alkoxy;

T is selected from hydrogen and
wherein $R_1$ is selected from hydrogen and $C_1$–$C_4$ alkyl; Q is a bivalent radical selected from —(CH$_2$)$_p$—, wherein p is an integer from 2 to 5, and —(CHR)$_p$—, wherein p is an integer from 2 to 5 and R is methyl or phenyl; and Z is selected from

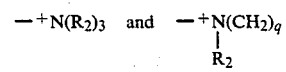

wherein $R_2$ may be the same or different and is selected from hydrogen and $C_1$-$C_4$ alkyl and q is an integer from 4 to 7.

4. A pharmaceutical composition of matter in dosage unit form comprising a compound, including the individual R and S enantiomers and racemic mixture, represented by the formula:

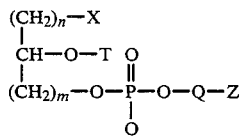

wherein n is an integer 1 or 2; m is an integer 1 or 2, and the sum of n and m must be 3; X is selected from the group consisting of $C_1$-$C_{24}$ branched or straight chain alkoxy and substituted phenoxy wherein the substituents are selected from one or more of the group consisting of $C_1$-$C_{20}$ branched or straight chain alkyl, $C_1$-$C_{20}$ branched or straight chain alkoxy, halogen, phenyl and substituted phenyl; T is selected from the group consisting of hydrogen and

wherein $R_1$ is selected from this group consisting of hydrogen, $C_1$-$C_4$ branched or straight chain alkyl, $C_1$-$C_4$ branched or straight chain alkoxy and $C_1$-$C_4$ branched or straight chain alkylamino; Q is a bivalent radical selected from the group consisting of —($CH_2$)$_p$— and —(CHR)$_p$—, where p is an integer from 2 to 12 and the moiety —(CHR)$_p$— represents an alkylene chain which is substituted by one or more $C_1$-$C_{10}$ alkyl groups or phenyl groups; and Z is selected from the group consisting of

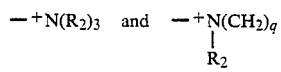

wherein $R_2$ may be the same or different and is selected from the group consisting of hydrogen and $C_1$-$C_4$ branched or straight chain alkyl and q is an integer from 4 to 7; in association with a pharmaceutically acceptable carrier.

5. A pharmaceutical composition of matter in dosage unit form comprising a compound, including the individual R and S enantiomers and racemic mixture in association with a pharmaceutically acceptable carrier, wherein said compound is represented by the formula:

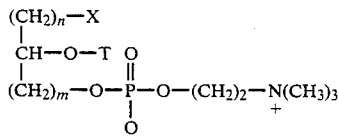

wherein n is an integer 1 or 2; m is an integer 1 or 2, and the sum of n and m must be 3; X is selected from n-hexadecyloxy, n-heptadecyloxy, n-octadecyloxy, n-pentadecyloxy, 4-tetradecylphenoxy, 3-tetradecylphenoxy, 2-tetradecylphenoxy, 3-tridecylphenoxy and 3-dodecyloxy-2-methyl phenoxy; and T is selected from hydrogen and acetyl.

6. A pharmaceutical composition of matter in dosage unit form comprising a compound, including the individual R and S enantiomers and racemic mixture, in association with a pharmaceutically acceptable carrier, wherein said compound is represented by the formula:

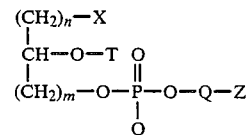

wherein n is an integer 1 or 2; m is an integer 1 or 2, and the sum of n and m must be 3; X is selected from $C_{11}$-$C_{19}$ alkoxy and substituted phenoxy wherein the substituents are selected from one or more of $C_1$-$C_{19}$ alkyl and $C_{11}$-$C_{15}$ alkoxy; T is selected from hydrogen and

wherein $R_1$ is selected from hydrogen and $C_1$-$C_4$ alkyl; Q is a bivalent radical selected from —($CH_2$)$_p$—, wherein p is integer from 2 to 5 and —(CHR)$_p$—, wherein p is an integer from 2 to 5 and R is methyl or phenyl; and Z is selected from

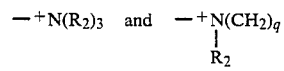

wherein $R_2$ may be the same or different and is selected from hydrogen and $C_1$-$C_4$ alkyl and q is an integer from 4 to 7.

7. Compounds, including the individual R and S enantiomers and the racemic mixtures, represented by the formula:

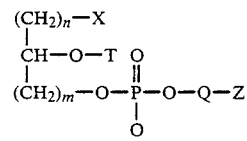

wherein n is an integer 1 or 2; m is an integer 1 or 2, and the sum of n and m must be 3; X is selected from the group consisting of $C_1$-$C_{24}$ branched or straight chain alkoxy and substituted phenoxy wherein the substituents are selected from one or more of the group consisting of $C_1$-$C_{20}$ branched or straight chain alkyl, $C_1$-$C_{20}$ branched or straight chain alkoxy, halogen, phenyl and substituted phenyl; t is selected from the group consisting of hydrogen and

wherein $R_1$ is selected from the group consisting of hydrogen, $C_1$-$C_4$ branched or straight chain alkyl, $C_1$-$C_4$ branched or straight chain alkoxy and $C_1$-$C_4$ branched or straight chain alkylamino; Q is a bivalent radical selected from the group consisting of —($CH_2$-

$)_p$— and —(CHR)$_p$—, where p is an integer from 2 to 12 and the moiety —(CHR)$_p$—, represents an alkylene chain which is substituted by one or more C$_1$-C$_{10}$ alkyl groups or phenyl groups; and Z is selected from the group consisting of —$^+N(R_2)_3$ and

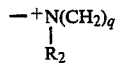

wherein R$_2$ may be the same or different and is selected from the group consisting of hydrogen and C$_1$-C$_4$ branched or straight chain alkyl and q is an integer from 4 to 7.

8. The compounds according to claim 7 wherein T is

9. The compounds according to claim 8, wherein Z is —N(CH$_3$)$_3$.

10. The compounds according to claim 9 wherein Q is —(CH$_2$)$_p$—.

11. The compounds according to claim 9 wherein n is 2 and m is 1.

12. The compounds according to claim 9 wherein n is 1 and m is 2.

13. The compounds according to claim 11 wherein T is

and p is 2.

14. The compounds according to claim 12, wherein T is

and p is 2.

15. The compounds according to claim 13 wherein X is C$_1$-C$_{24}$ branched or straight chain alkoxy.

16. The compounds according to claim 14 wherein X is C$_1$-C$_{24}$ branched or straight chain alkoxy.

17. Compounds, including the individual R and S enantiomers and the racemic mixture, represented by the formula:

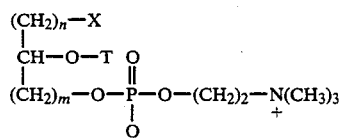

wherein n is an integer 1 or 2; m is an integer 1 or 2, and the sum of n and m must be 3; X is selected from n-hexadecyloxy, n-heptadecyloxy, n-octadecyloxy, n-pentadecyloxy, 4-tetradecylphenoxy, 3-tetradecylphenoxy, 2-tetradecylphenoxy, 3-tridecylphenoxy and 3-dodecyloxy-2-methyl phenoxy; and T is selected from hydrogen and acetyl.

18. Compounds, including the individual R and S enantiomers and the racemic mixtures, represented by the formula:

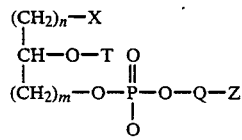

wherein n is an integer 1 or 2; m is an integer 1 or 2, and the sum of n and m must be 3; X is selected from C$_{11}$-C$_{19}$ alkoxy and substituted phenoxy wherein the substituents are selected from one or more of C$_1$-C$_{19}$ alkyl and C$_{11}$-C$_{15}$ alkoxy; T is selected from hydrogen and

wherein R$_1$ is selected from hydrogen and C$_1$-C$_4$ alkyl; Q is a bivalent radical selected from —(CH$_2$)$_p$—, wherein p is an integer from 2 to 5, and —(CHR)$_p$—, wherein p is an integer from 2 to 5 and R is methyl or phenyl; and Z is selected from

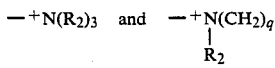

wherein R$_2$ may be the same or different and is selected from hydrogen and C$_1$-C$_4$ alkyl and q is an integer from 4 to 7.

* * * * *